United States Patent
Oikawa et al.

(10) Patent No.: US 9,633,814 B2
(45) Date of Patent: Apr. 25, 2017

(54) X-RAY CT APPARATUS (71) Applicant: TOSHIBA MEDICAL SYSTEMS CORPORATION, Otawara-Shi (JP)

(72) Inventors: Daizo Oikawa, Otawara (JP); Fumio Ishiyama, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 89 days.

(21) Appl. No.: 14/288,753

(22) Filed: May 28, 2014

(65) Prior Publication Data

US 2014/0270055 A1    Sep. 18, 2014

Related U.S. Application Data (63) Continuation of application No. PCT/JP2013/075921, filed on Sep. 25, 2013.

(30) Foreign Application Priority Data

Sep. 26, 2012  (JP) .................................. 2012-212135

(51) Int. Cl.
*H01J 35/02* (2006.01)
*H01J 37/24* (2006.01)
(Continued)

(52) U.S. Cl.
CPC ............ *H01J 35/025* (2013.01); *A61B 6/405* (2013.01); *G05F 1/565* (2013.01); *H01J 37/241* (2013.01);
(Continued)

(58) Field of Classification Search
CPC ....... A61B 6/032; A61B 6/405; A61B 6/4241; A61B 6/542; A61B 6/4021; A61B 6/4291;
(Continued)

(56) References Cited

U.S. PATENT DOCUMENTS

2006/0109951 A1   5/2006 Popescu
2009/0304249 A1   12/2009 Wu
(Continued)

FOREIGN PATENT DOCUMENTS

CN   1765327 A    5/2006
CN   101598686 A   12/2009
(Continued)

OTHER PUBLICATIONS

International Search Report mailed Jan. 7, 2014 for PCT/JP2013/075921 filed Sep. 25, 2013 with partial English Translation.
(Continued)

*Primary Examiner* — Anastasia Midkiff
(74) *Attorney, Agent, or Firm* — Oblon, McClelland, Maier & Neustadt, L.L.P.

(57) ABSTRACT

X-ray CT apparatus is provided in which the photon energy distribution of X-rays to be radiated is flattened. X-ray CT apparatus includes an X-ray tube, a detector, a data acquisition system, a tube voltage generator, and a grid controller. The X-ray tube radiates X-rays onto a subject. The detector includes multiple detection elements for detecting photons forming the X-rays. The data acquisition system counts the number of the detected photons to acquire projection data based on the counted photons. The tube voltage generator applies the tube voltage to the X-ray tube while changing the tube voltage of the X-ray tube in a predetermined cycle. A tube current controller decreases the tube current upon an increase in the tube voltage, and increases the tube current upon a decrease in the tube voltage. Thus, the photon energy distribution of the X-rays radiated from the X-ray tube is flattened.

5 Claims, 7 Drawing Sheets (51) Int. Cl.
*H05G 1/32* (2006.01)
*H05G 1/46* (2006.01)
*G05F 1/10* (2006.01)
*G05F 1/56* (2006.01)
*G05F 1/565* (2006.01)
*H01J 37/302* (2006.01)
*H01J 37/248* (2006.01)
*A61B 6/00* (2006.01)
*A61B 6/03* (2006.01)

(52) U.S. Cl.
CPC ........ *H01J 37/248* (2013.01); *H01J 37/3023* (2013.01); *H05G 1/32* (2013.01); *H05G 1/46* (2013.01); *A61B 6/032* (2013.01); *A61B 6/4241* (2013.01); *A61B 6/54* (2013.01); *A61B 6/542* (2013.01); *A61B 6/58* (2013.01); *G05F 1/10* (2013.01); *H01J 2237/2487* (2013.01)

(58) Field of Classification Search
CPC ..... A61B 6/4441; A61B 6/482; A61B 6/5217; A61B 6/5252; A61B 6/4405; A61B 6/4452; A61B 6/4458; A61B 6/4464; A61B 6/547; A61B 6/00; A61B 6/02; A61B 6/03; A61B 6/40; A61B 6/42; A61B 6/4208; A61B 6/48; A61B 6/54; A61B 6/58; A61B 34/00; A61B 34/10; A61B 2090/00; A61B 2090/36; A61B 2090/37; A61B 2090/376; A61B 2090/3762; A61B 2560/00; A61B 2560/02; A61B 2560/0204; A61B 2560/0214; A61B 2560/06; A61B 2576/00; H05G 1/30; H05G 1/46; H05G 1/00; H05G 1/08; H05G 1/085; H05G 1/26; H05G 1/265; H05G 1/32; G05F 1/00; G05F 1/10; G05F 1/46; G05F 1/56; G05F 1/565; G05F 1/625; G05F 1/66; G05F 1/70; G05F 5/00; H01J 35/00; H01J 35/02; H01J 35/025; H01J 37/00; H01J 37/24; H01J 37/241–37/243; H01J 37/248; H01J 37/30; H01J 37/3002; H01J 37/302; H01J 37/3023; H01J 37/304; H01J 2235/00; H01J 2235/02; H01J 2237/00; H01J 2237/248; H01J 2237/2485; H01J 2237/2487
USPC .............................................. 378/4, 9, 16, 62
See application file for complete search history.

(56) References Cited

U.S. PATENT DOCUMENTS

2010/0183117 A1* 7/2010 Tsumuraya ............ A61B 6/405
378/9
2010/0303196 A1 12/2010 Zou

FOREIGN PATENT DOCUMENTS

| CN | 101897595 A | 12/2010 |
|---|---|---|
| JP | 2006-122679 A | 5/2006 |
| JP | 2009-082173 A | 4/2009 |
| JP | 2009-268899 A | 11/2009 |
| JP | 2009-294209 A | 12/2009 |
| JP | 2010-247108 | 12/2010 |
| JP | 2012-033411 A | 2/2012 |
| JP | 2012-034901 A | 2/2012 |
| JP | 2012-090887 A | 5/2012 |

OTHER PUBLICATIONS

Combined Chinese Office Action and Search Report issued Oct. 30, 2015 in Patent Application No. 201380004673.8 (with English translation of Categories of Cited Documents).
Office Action mailed Jul. 26, 2016 in Japanese Application No. 2012-212135 filed Sep. 26, 2012.

* cited by examiner

X-RAY CT APPARATUS

CROSS-REFERENCE TO RELATED APPLICATION

This application is based upon and claims the benefit of priority from Japanese Patent Applications No. 2012-212135 filed on Sep. 26, 2012; the entire contents of which are incorporated herein by reference.

FIELD

The present embodiment relates to an X-ray CT apparatus.

BACKGROUND

An X-ray computed tomography system (hereinafter, referred to as an "X-ray CT apparatus") radiates X-rays onto a subject, detects the X-rays transmitted through the subject, and thereby obtains projection data reflecting coefficients of X-ray absorption within the subject.

Also, in recent years, X-ray CT apparatuses (hereinafter, also referred to as "photon counting CTs") using detectors of the photon counting method have been developed. The photon counting CTs are different from conventional X-ray CT apparatuses using integral-mode detectors in that the former classify and count the energy of X-rays (photons) incident on the detectors in detecting X-rays radiated from an X-ray tube and transmitted through the subject. Thereby, it becomes possible to enable the transmittance of each part of the subject in addition to the separation of elements of the subject.

X-rays radiated from an X-ray tube include characteristic X-rays and braking X-rays. Characteristic X-rays have an energy distribution which depends on the target material, while braking X-rays have a continuous energy distribution. It should be noted that this energy distribution shows the relationship between the volume of energy and the number of photons (that is, the dose of X-rays). In photon counting CTs, braking X-rays are mainly used for making diagnoses. Braking X-rays are characterized in that the photon energy distribution varies depending on the voltage applied to the X-ray tube, with the upper limit thereof restricted by the voltage (namely, the tube voltage) applied to the X-ray tube.

On the other hand, the photon energy distribution of X-rays generated from X-ray tubes has a large deviation. In other words, the dose (namely, the X-ray intensity) differs depending on the volume of energy. Therefore, if the tube voltage is too low, sufficient photons for making a diagnosis may not be obtained in an energy region (hereinafter, referred to as an "energy band") with a small dose. In addition, an increase in the tube voltage for obtaining photons necessary for a diagnosis may cause excess exposure in an energy band with a large dose. Therefore, with the photon counting CTs, it is required to widen the energy band covering the distribution of photons and reduce the dose of X-rays, namely, to flatten the energy distribution of photons (hereinafter, referred to as the "photon energy distribution").

DETAILED DESCRIPTION

An X-ray CT apparatus is provided in which the photon energy distribution of X-rays to be radiated is flattened.

In order to achieve the abovementioned object, the embodiments consist of an X-ray CT apparatus including an X-ray tube, a detector, a data acquisition system, a tube voltage generator, and a grid controller. The X-ray tube radiates X-rays onto a subject. The detector includes multiple detection elements for detecting photons forming the X-rays. The data acquisition system counts the number of the detected photons to acquire projection data based on the counted photons.

The tube voltage generator applies the tube voltage to the X-ray tube while changing the tube voltage of the X-ray tube in a predetermined cycle. A tube current controller decreases the tube current upon an increase in the tube voltage, and increases the tube current upon a decrease in the tube voltage. In this X-ray CT apparatus, the photon energy distribution of the X-rays radiated from the X-ray tube is flattened.

First Embodiment

Figure 1:
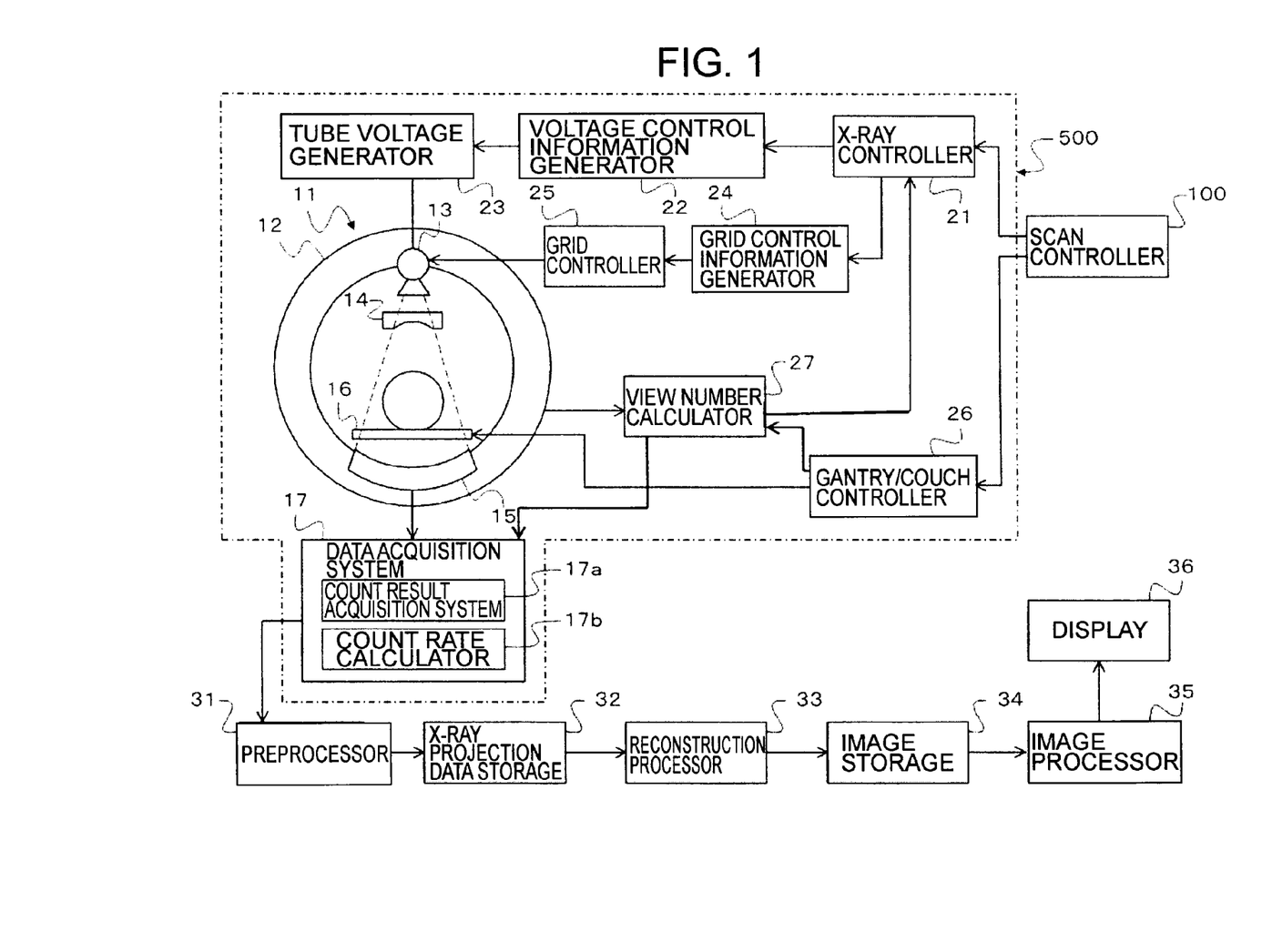
FIG. 1 is a block diagram illustrating the configuration of an X-ray CT apparatus according to a first embodiment.

The configuration of an X-ray CT apparatus according to a first embodiment will be described with reference to FIG. 1. As illustrated in the block diagram in FIG. 1, the X-ray CT apparatus according to the present embodiment includes an imaging unit 500, a scan controller 100, a preprocessor 31, an X-ray projection data storage 32, a the reconstruction processor 33, an image storage 34, an image processor 35, and a display 36.

(Imaging Unit 500)

The imaging unit 500 includes a gantry 11, a tube voltage generator 23, an X-ray controller 21, a voltage control information generator 22, a grid controller 25, a grid control information generator 24, and a gantry/couch controller 26. The gantry 11 includes a rotating gantry 12, an X-ray source (X-ray tube) 13, an X-ray filter 14, an X-ray detector 15, a sliding couch 16, a data acquisition system 17, and the scan controller 100. The X-ray detector 15 is an array-type X-ray detector. That is, in the X-ray detector 15, detection elements are arranged in the matrix form of m rows in the channel direction and n columns in the slice direction.

In this embodiment, an X-ray tube (triode) with an anode, a cathode (or a heater), and a grid is used as the X-ray source 13. The X-ray source 13 and the X-ray detector 15 are placed on the rotating gantry 12, and disposed opposite to each other by interposing a subject lying on the sliding couch 16. Each channel is associated with each of the detection elements of the X-ray detector 15. The X-ray source 13 faces the subject via the X-ray filter 14.

The scan controller 100 serves as the control center of all systems, controlling the X-ray controller 21, the gantry/couch controller 26, and the sliding couch 16 based on predetermined acquisition conditions (hereinafter, also referred to as "scan conditions") of projection data. The scan conditions include information (control parameters) for radiating X-rays with the desired intensity at the desired timing, such as a tube voltage (more specifically, the voltage between the anode and the cathode), a tube current (more specifically, an anode current), an X-ray radiation period, and a view number. That is, the scan controller 100 rotates the rotating gantry 12 along a predetermined path around the subject while radiating X-rays from the X-ray source 13. It should be noted that the resolution of projection data is decided based on the predetermined scan conditions. That is, according to the required resolution, scan conditions are predetermined, and the scan controller 100 controls the operation of each part based on the scan conditions.

In addition, when instructed to stop scanning, the scan controller 100 controls the X-ray controller 21, the gantry/couch controller 26, and the sliding couch 16, and stops imaging. This instruction serves as a trigger for the scan controller 100 to automatically stop scanning.

The X-ray controller 21 receives information indicating the scan conditions from the scan controller 100. The X-ray controller 21 outputs, to a view number calculator 27, information indicating the view number per one rotation of the gantry, among the above information. The X-ray controller 21 also receives, from the view number calculator 27, a synchronization pulse for synchronizing the rotation of the rotating gantry 12 (the synchronization pulse will be described later). Based on this synchronization pulse, the X-ray controller 21 controls the radiation timing of X-rays so as to synchronize the timing with the rotation of the rotating gantry 12.

Further, the X-ray controller 21 determines the radiation timing of the X-rays including the control timing for changing the tube voltage so as to synchronize the received synchronization pulse. The X-ray controller 21 manages the radiation conditions of the X-rays among the information indicating the scan conditions, specifically, manages information indicating the tube voltage including its range of change, the tube current, and the radiation period of the X-rays, as well as the determined radiation timing, as information indicating the radiation conditions. The photon energy distribution of the X-rays to be radiated is determined based on the radiation conditions. In the X-ray CT apparatus according to the present embodiment, the tube voltage is changed every one cycle in a predetermined cycle of the synchronization pluse, whereby the range of the photon energy distribution is widened. It should be noted that the photon energy distribution is the distribution of photon integrated values per one cycle in the abovementioned predetermined cycle. Further, this X-ray CT apparatus accordingly controls the grid voltage to decrease the tube current upon an increase in the tube voltage and increase the tube current upon a decrease in the tube voltage, thereby always providing the X-ray intensity in a predetermined range. That is, the information indicating the radiation conditions of the X-rays includes information indicating the control timing of the tube voltage along the time sequence, along with information indicating the control timing of the grid voltage for changing the tube current in synchronization with the control timing of the tube voltage (the same as the control timing of the tube voltage in terms of the time sequence). It should also be noted that the relationship between the details of the control timing of the tube voltage, tube current, and grid voltage, and the photon energy distribution will be described later.

In order to flatten the photon energy distribution, the X-ray controller 21 outputs information for controlling the tube voltage among the information indicating the radiation conditions of the X-rays (for example, the change in the tube voltage along the control timing in terms of the time sequence, and the change cycle) to the voltage control information generator 22. The voltage waveform by which the voltage control information generator 22 and the tube voltage generator 23 control the tube voltage changes as illustrated in Graph G11 in FIG. 2B (details will be described later).

Further, based on information for controlling the tube current among the information indicating the radiation conditions of the X-rays, the X-ray controller 21 generates information for controlling the grid voltage (for example, the change in the grid voltage along the control timing in terms of the time sequence, and the change cycle).

Figure 2A:
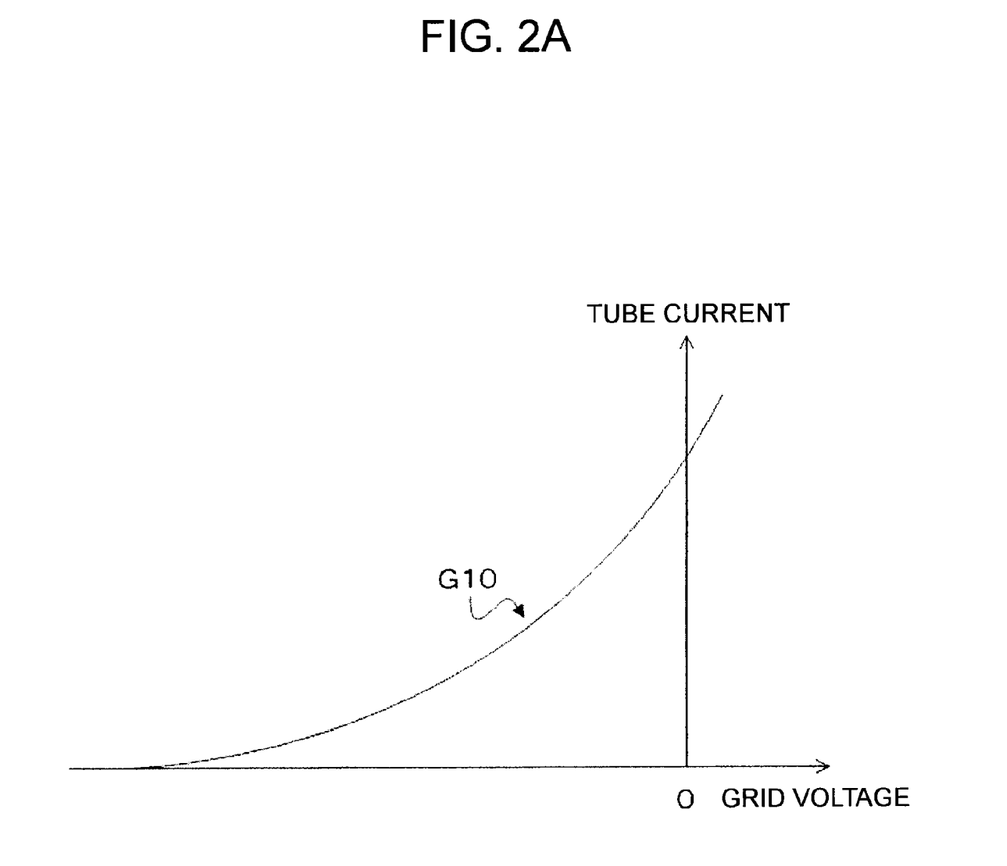
FIG. 2A is a graph illustrating the characteristics of the tube current with respect to the grid voltage.
Figure 2B:
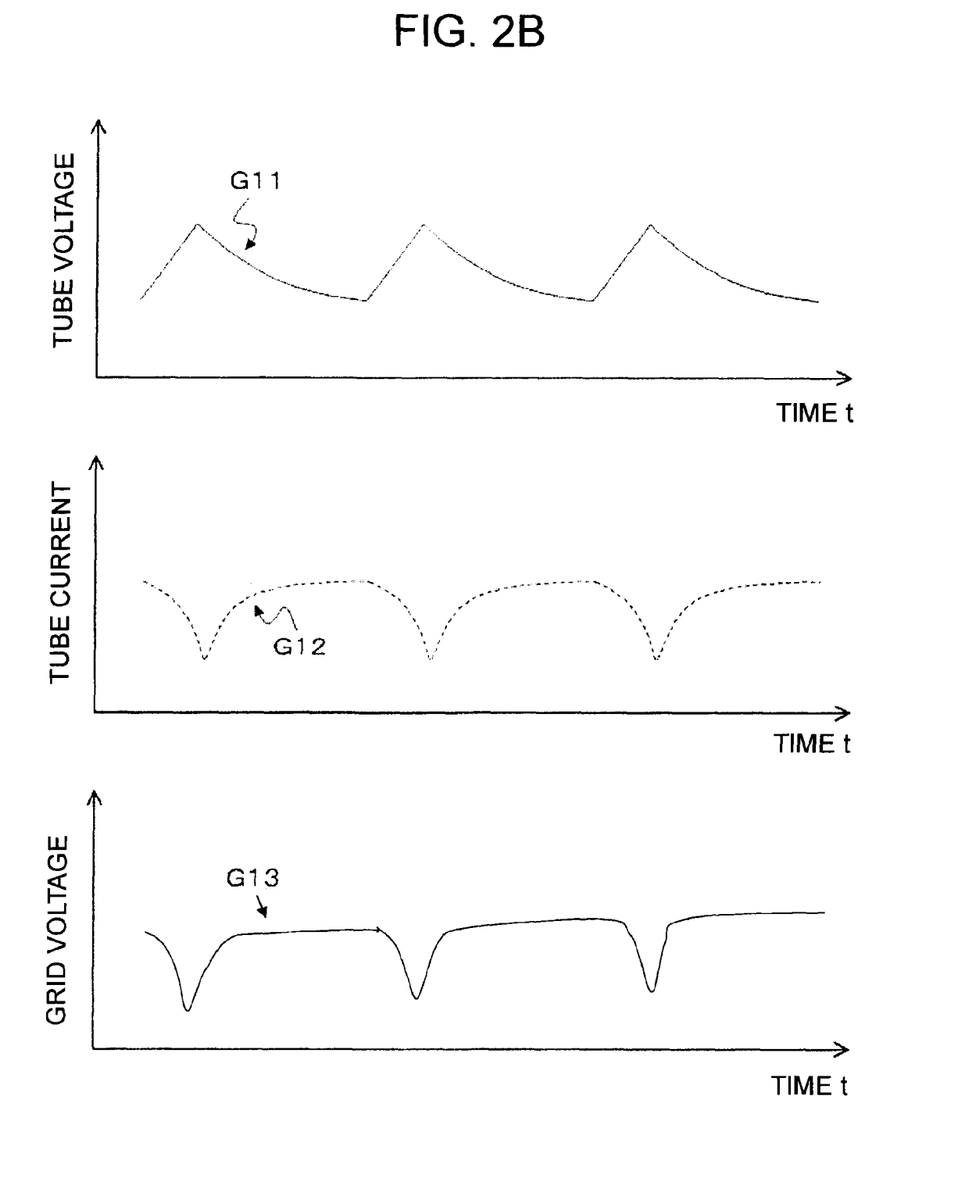
FIG. 2B is a diagram describing the control timing of the tube voltage, tube current, and grid voltage, respectively.

Here, in the X-ray CT apparatus according to the present embodiment, when the tube voltage generator 23 applies, to the X-ray source 13, a tube voltage that changes as illustrated in Graph G11 in FIG. 2B, for example, the tube current exponentially increases in response to an increase in the tube voltage. Then, in the X-ray CT apparatus according to the present embodiment, a tube current that offsets the change in the tube current caused by the change in the tube voltage needs to be generated.

Subsequently, the X-ray controller 21 carries out the following (a), (b), and (c) to generate information for controlling a grid. (a) The change in the tube current with respect to the change in the tube voltage is preliminarily specified based on the characteristics of the X-ray source 13. (b) Even if there is a change in the tube current due to the change in the tube voltage, as it is necessary to offset the change in the tube current to control so as to make the actual tube current always coincide with information regarding the control of the tube current shown as the radiation conditions, the change in the tube current that offsets the change in the tube current occurring corresponding to the change in the tube voltage is specified. One example of the pattern of offsetting the change in the tube current is seen in Graph G12 in FIG. 2B (details will be described later). The characteristics in Graph G12 illustrate increase and decrease countertendencies to increases and decreases in the tube voltage in Graph G11. (c) Further, in order to obtain the tube current in Graph G12 in FIG. 2B, grid voltage-tube current characteristics (tube voltage parameters) of the X-ray source 13 are stored beforehand, and from the grid voltage-tube current characteristics, information indicating the change in the grid voltage for obtaining the change in the tube current in Graph G12 in FIG. 2B is specified. The X-ray controller 21 then outputs the specified change in the grid voltage to the grid control information generator 24.

Here, the grid voltage-tube current characteristics (tube voltage parameters) of the X-ray source 13 will be described. First, refer to FIG. 2A. Graph G10 shown in FIG. 2A is a graph illustrating one example of the characteristics of the X-ray source 13, namely, one example of the characteristics of the tube current with respect to the grid voltage for the case in which the tube voltage is constant. The grid voltage in FIG. 2A is the voltage with respect to a cathode, and this grid voltage is usually used in voltage regions on the negative side in the vicinity of zero. Hence, if normal operations are specific voltages (bias voltages) in a negative region, the grid voltage is increased in the positive direction (0 voltage direction in FIG. 2A) when an increase in the tube current (dose) is desired; whereas, the grid voltage is increased in the negative direction (direction opposite to the 0 voltage direction in FIG. 2A) when a decrease in the tube current (dose) is desired. These characteristics illustrated in Graph G10 are preliminarily investigated and stored in the X-ray controller 21 as information. Based on this information and the information regarding the control of the tube current, the X-ray controller 21 only has to generate the information for controlling the grid voltage.

The voltage control information generator 22 receives the information for controlling the tube voltage (the tube voltage and its range of change, along with the control timing) from the X-ray controller 21. Based on this information, the voltage control information generator 22 generates a control waveform pattern (hereinafter, referred to as an "output voltage waveform pattern") for controlling the tube voltage of the X-ray source 13. Here, refer to FIG. 2B. Graph G11 in FIG. 2B illustrates an output voltage waveform pattern for widening the range of the photon energy distribution. The voltage control information generator 22 outputs the generated output voltage waveform pattern to the tube voltage generator 23. Based on this output voltage waveform pattern, the tube voltage generator 23 applies a tube voltage to the X-ray source 13, and changes its voltage value along the time sequence.

The grid control information generator 24 receives the information for controlling the grid voltage from the X-ray controller 21. Based on this information, the grid control information generator 24 generates a control waveform pattern (hereinafter, referred to as a "grid control voltage waveform pattern") for controlling the grid voltage of the X-ray source 13. As mentioned above, it is necessary to generate a tube current so as to offset the change in the tube current due to the change in the tube voltage. One example of the change in the tube current for the offsetting is Graph G12 in FIG. 2B. Therefore, the grid control information generator 24 generates Graph G13 having a grid control voltage waveform pattern so as to cause the change in the tube current of Graph G12 in FIG. 2B, and outputs the Graph 13 to the grid control information generator 24. Based on Graph G13 having the grid control voltage waveform pattern, the grid controller 25 controls the grid voltage (control information). Thus, the grid control information generator 24 and the grid controller 25 controls the grid voltage to decrease the tube current upon an increase in the tube voltage and increase the tube current upon a decrease in the tube voltage, thereby decreasing the change in the tube current caused by the change in the tube voltage. The grid controller 25 is one example of a "tube current controller."

It should be noted that in the description of operations regarding the grid voltage-tube current characteristics based on FIG. 2A and FIG. 2B, the grid controller 25 inputs the change in the grid voltage as in Graph G13 having a grid control voltage waveform pattern, as a grid voltage on the horizontal axis in FIG. 2A. The change in the grid voltage is converted into the change in the tube current of the vertical axis by the characteristics of Graph G10 in FIG. 2A to output.

As mentioned so far, the tube voltage generator 23 applies a tube voltage to the X-ray source 13, the grid controller 25 controls the grid voltage, and thereby the X-rays are radiated from the X-ray source 13.

Beforehand, the view number calculator 27 receives control information indicating the view number per one rotation of the gantry via the scan controller 100 and the gantry/couch controller 26. In addition, an encoder (not illustrated) is provided in the rotating gantry 12, which detects the rotational position of the rotating gantry 12 and outputs pulse signals to the view number calculator 27. The view number calculator 27 receives the pulse signals from the encoder, converts the signals into the view number per second based on the rotational speed of the rotating gantry 12 and the control information indicating the view number per one rotation of the gantry, and generates a synchronization pulse to synchronize with the rotation of the rotating gantry 12. Thus, one example of the specific configuration of the view number calculator 27 for synchronizing with the rotation of the rotating gantry 12 is a PLL (Phase-Locked Loop) circuit. The view number calculator 27 outputs the generated synchronization pulse to the X-ray controller 21 and the data acquisition system 17. Thereby, both the X-ray controller 21 and the data acquisition system 17 can operate respectively in synchronization with the rotation of the rotating gantry 12.

The X-ray detector 15 includes the multiple detection elements of the photon counting method for counting light (photon) derived from the X-rays that have been transmitted through the subject. One example is that the detection elements of the X-ray detector 15 according to Example 1 are made of cadmium telluride (CdTe). Namely, the X-ray detector 15 is a direct conversion semiconductor detector that counts light derived from the X-rays by directly converting the incident X-rays into light by those detection elements.

It should be noted that hereinafter, the case in which the X-ray detector 15 is a direct conversion semiconductor detector will be described; however, the present embodiment can be operated even for the case in which the X-ray detector 15 is configured by a scintillator, a light guide, or a photomultiplier tube. In addition, the X-ray detector 15 according to the present embodiment can be operated not only in counting light derived from the X-rays that have been transmitted through a subject P, but also in discriminating energy values of the transmitted X-rays.

The data acquisition system 17 receives synchronization pulses from the view number calculator 27. In synchronization with these synchronization pulses, the data acquisition system 17 acquires the count results of the X-ray detector 15, and also carries out an arithmetic process on the count results of the X-ray detector 15. More specifically, as illustrated in FIG. 1, the data acquisition system 17 includes a count result acquisition system 17a and a count rate calculator 17b.

The count result acquisition system 17a acquires the count results obtained by detecting and counting light derived from the individual X-rays which have been transmitted through the subject P by the X-ray detector 15, its detection period (count period), and the detection position (the position of the detection elements), in synchronization with the synchronization pulse. The count result acquisition system 17a then outputs the acquired count results to the count rate calculator 17b. It should be noted that if the X-ray detector 15 can discriminate energy values, the count result acquisition system 17a acquires the detection period, the energy value the X-rays, and the detection position, as the count results, in synchronization with the synchronization pulse, and outputs the acquired count results to the count rate calculator 17b mentioned later.

The count rate calculator 17b receives the count results from the count result acquisition system 17a. Based on the count results, the count rate calculator 17b calculates a value (count rate) indicating how many times each detection element of the X-ray detector 15 counts the light derived from the X-rays per unit time. The count rate calculator 17b transmits count information indicating the calculated value to the preprocessor 31.

The preprocessor 31 carries out correction processing, such as logarithmic transformation processing, offset correction, sensitivity correction, and beam hardening correction, on the count information transmitted from the count result acquisition system 17a, thereby generating projection data. The preprocessor 31 stores the generated projection data in the X-ray projection data storage 32.

The X-ray projection data storage 32 stores the projection data generated by the preprocessor 31. That is, the X-ray projection data storage 32 stores projection data for generating scanograms, as well as projection data for reconstructing X-ray CT images.

The reconstruction processor 33 carries out back projection processing (for example, back projection processing by the FBP (Filtered Back Projection) method) on X-ray CT images for reconstruction stored in the X-ray projection data storage 32, thereby reconstructing image data. The reconstruction processor 33 stores the reconstructed image data in the image storage 34. The reconstruction processor 33 also generates scanograms from projection data for generating scanograms stored in the X-ray projection data storage 32, and stores the generated scanograms in the image storage 34.

The image processor 35 reads the image data from the image storage 34. Based on the image data, the image processor 35 generates images, such as tomographic images, and static images or motion images of 3D images. The image processor 35 causes the display 36 to display the generated images.

It should be noted that, as mentioned above, the example of the X-ray controller 21 for controlling the timing of switching the tube voltage based on synchronization pulses from the view number calculator 27 has been described. However, if the cycle of switching the tube voltage is sufficiently shorter than the data acquisition cycle, it is not always necessary to synchronize the cycle of switching the tube voltage with synchronization pulses. The case in which the repetition frequency of the change of the tube voltage (namely, the cycle of switching the tube voltage) is not identical to the repetition frequency of data acquisition (namely, the data acquisition cycle) causes variations in the integrated values of the photon energy distribution of each data acquisition period. However, for example, if the repetition frequency of the change of the tube voltage is over 10 times higher than the repetition frequency of data acquisition, variations become sufficiently small with respect to the integrated values and can be ignored. Therefore, in such the case, the X-ray controller 21 does not always need to synchronize the cycle of switching the tube voltage with synchronization pulses from the view number calculator 27.

(Photon Energy Distribution)

Figure 3A:
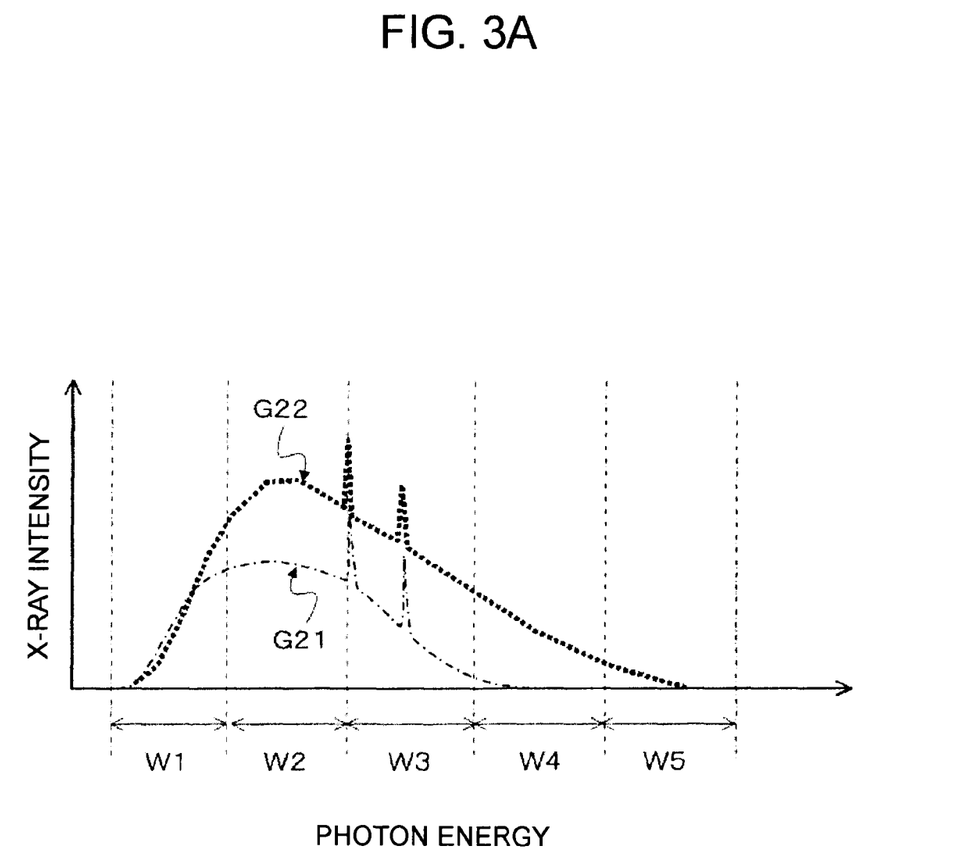
FIG. 3A is a graph describing the relationship between changes in the tube voltage and the photon energy distribution.

Hereinafter, referring to FIG. 3A, the relationship between the control in the tube voltage, tube current, and grid voltage, and the photon energy distribution will be described. FIG. 3A is a graph describing the relationship between the change in the tube voltage and the photon energy distribution.

First, referring to FIG. 3A, the relationship between the change in the tube voltage and the photon energy distribution will be described. In FIG. 3A, the horizontal axis represents the photon energy, while the vertical axis represents the X-ray intensity of the energy (that is, the number of photons). Each of W1 to W5 in FIG. 3A indicates an energy band, with the number of photons counted in each region. Further, Graph G21 illustrates the photon energy distribution in the case of a low tube voltage (in the case of a low voltage). Also, Graph G22 illustrates the photon energy distribution in the case of a high tube voltage (in the case of a high voltage). The X-ray intensity increases in proportion to the number of photons. In short, an energy band with a high X-ray intensity indicates a large number of photons.

The photon energy distribution of the X-rays radiated from the X-ray source 13 changes depending on the tube voltage. More specifically, when the tube voltage is low, the average energy value is decreased and so is the maximum energy value of the braking X-rays. On the other hand, when the tube voltage is high, the average energy value of the X-rays (energy with photons) is increased and so is the maximum energy value of the braking X-rays. That is, the maximum photon energy of the braking X-rays depends on the tube voltage. Subsequently, the X-ray CT apparatus according to the present embodiment changes the tube voltage during the data acquisition period in order to disperse the photon energy distribution of the X-rays.

However, an increase in the tube voltage results in a change in the photon energy distribution of the braking X-rays and simultaneously in a large increase in the dose rate to be radiated (the dose rate is in proportion to the square of the tube voltage). Therefore, if the energy distribution during the tube voltage change period is integrated, the energy distribution upon a high tube voltage will be dominant, and largely preventing the effect of flattening the photon energy distribution from being exerted. Then, the X-ray CT apparatus according to the present embodiment changes the tube current simultaneously as the tube voltage is changed. The dose rate is in proportion to the tube current, thereby, the tube current is controlled to be large upon a low tube voltage and to be low upon a high tube voltage. Consequently, the dose rate is controlled to be constant even upon changes in the tube voltage, thereby allowing the photon energy distribution of the braking X-rays to be flattened.

It should be noted that one general method for controlling the tube current is a method for controlling the filament current of the X-ray tube and controlling the amount of thermo electrons emitted from the cathode of the X-ray source 13. However, by this method, the thermal response delay of the filament cannot lead to a high-speed change in the tube current. For example, for the case in which the rotation speed of the rotating gantry 12 is 120 rpm and the View number per one rotation of the gantry is 900, the respectively indicate view number per second will be 1800, with the data acquisition period as short as 555.6 microseconds, far shorter than the thermal response delay period (tens of milliseconds) of the filament. Therefore, in the X-ray CT apparatus according to the present embodiment, as a method for controlling the tube current, the method for controlling the grid voltage of the X-ray source 13 is adopted.

The application of a negative voltage to the X-ray tube grid enables the amount of electrons emitted from the cathode to be controlled to decrease, as in the case of the triode vacuum tube. First, when the grid voltage is zero, the tube current is preliminarily adjusted by the filament current, and high-speed changes in the tube current during the data acquisition period is controlled by the grid voltage. It should be noted that since the magnitude of the tube current changes depending on the subject thickness, diagnostic region, diagnostic purpose, and scan conditions, the filament current value may be determined based on these set conditions.

(Changes and Control Timings of Tube Voltages, Tube Currents, Grid Voltages)

Figure 3B:
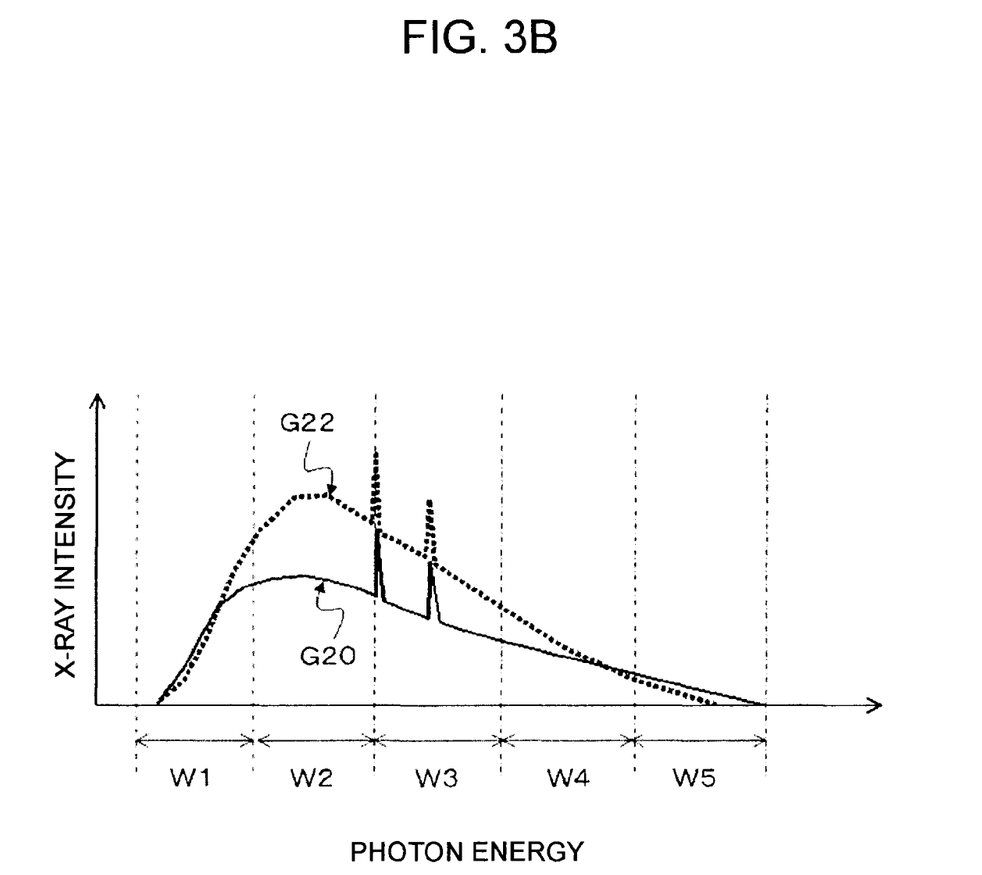
FIG. 3B is a graph illustrating one example of the photon energy distribution in the X-ray CT apparatus according to the present embodiment.

Hereinafter, the control timing of tube voltages, tube currents, and grid voltages will be described in detail, with reference to FIG. 2B and FIG. 3B. FIG. 3B is a graph illustrating one example of the photon energy distribution in the X-ray CT apparatus according to the present embodiment.

As mentioned above, in the X-ray CT apparatus according to the present embodiment, the tube voltage is changed per one cycle in a predetermined cycle. For example, Graph G11 having the output voltage waveform pattern in FIG. 2B illustrates changes in the tube voltage along the time sequence, and the cycle of the change in the tube voltage synchronizes the rotation of the rotating gantry 12 caused by synchronization pulses from the view number calculator 27. In addition, the tube current shown in Graph G12 is a tube current controlled by the grid voltage shown in Graph G13 having the grid control voltage waveform pattern. As illustrated in Graph G12, the tube current is controlled in synchronization with changes in the tube voltage such that the tube current decreases upon an increase in the tube voltage and increases upon a decrease in the tube voltage.

Here, refer to FIG. 3B. FIG. 3B is a graph illustrating one example of the photon energy distribution in the X-ray CT apparatus according to the present embodiment. Graph G22 in FIG. 3B corresponds to Graph G22 in FIG. 3A. In addition, Graph G20 illustrates one example of the photon energy distribution in the X-ray CT apparatus according to the present embodiment. As illustrated in FIG. 3B, the X-ray CT apparatus according to the present embodiment changes the tube voltage along the time sequence, thereby widening the photon energy distribution of the braking X-rays in comparison with Graph G22, and controlling the tube current in synchronization with the changes in the tube voltage. As a result, as illustrated in Graph G20, in comparison with Graph G22, the X-ray CT apparatus controls the photon energy distribution of the braking X-rays to be flattened. Namely, the photon energy distribution is flattened.

As described above, the X-ray CT apparatus according to the present embodiment widens the photon energy distribution of the braking X-rays by changing the tube voltage along the time sequence. In addition, the X-ray CT apparatus according to the present embodiment controls the grid voltage corresponding to changes in the tube voltage, thereby changing the tube voltage in synchronization with the changes in the tube voltage. More specifically, the tube current is decreased upon an increase in the tube voltage and the tube current is increased upon a decrease in the tube voltage. Thus, the X-ray CT apparatus according to the present embodiment controls the photon energy distribution of braking X-rays so as to be flattened. That is, the photon energy distribution is flattened, allowing the photon energy distribution to be widened and preventing unnecessary exposure upon an increase in the tube voltage.

Second Embodiment

Figure 4:
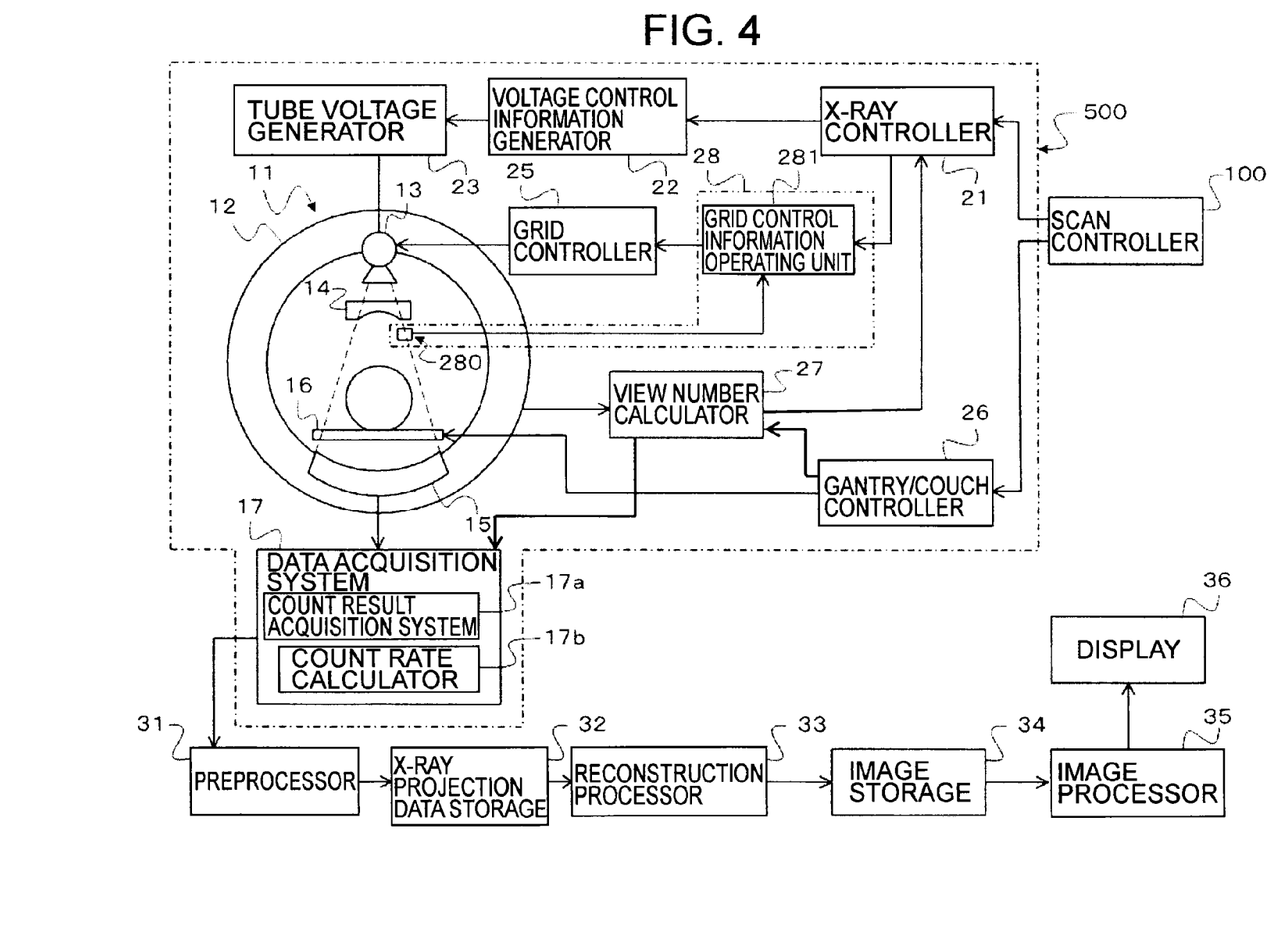
FIG. 4 is a block diagram illustrating the configuration of an X-ray CT apparatus according to a second embodiment.

Hereinafter, the configuration of an X-ray CT apparatus according to a second embodiment will be described. In the first embodiment, in synchronization with the control timing of the tube voltage, the grid control voltage waveform pattern G13 controls the tube current to synchronize the change in the tube current with the change in the tube voltage, and maintains the dose rate within a predetermined range. That is, in order for the intensity of X-rays radiated from the X-ray source 13 to be maintained within a predetermined range, the grid voltage is controlled and thereby the intensity of the X-rays is indirectly controlled. The X-ray CT apparatus according to the present embodiment measures the dose of the X-rays radiated from the X-ray source 13, the measurement results are fed back, and thereby, the dose of the X-rays is controlled to maintain the dose to be within a predetermined range. Hereinafter, with reference to FIG. 4, the second embodiment will be described focusing on points different from the first embodiment. FIG. 4 is a block diagram illustrating the configuration of the X-ray CT apparatus according to the present embodiment.

The X-ray CT apparatus according to the present embodiment uses a grid control information generator 28, instead of the grid control information generator 24. The grid control information generator 28 includes a measuring unit 280 and a grid control information operating unit 281.

The gantry/couch controller 26 receives control information indicating the scan conditions from the scan controller 100. The gantry/couch controller 26 specifies the view number per one rotation of the gantry based on this control information, and outputs information indicating this to the view number calculator 27. As mentioned above, based on the rotational speed of the rotating gantry 12 and the view number per one rotation of the gantry, the view number calculator 27 converts the information to the view number per second, and generates a synchronization pulse to synchronize with the rotation of the rotating gantry 12. Subsequently, the X-ray controller 21 receives, from the view number calculator 27, the synchronization pulse to synchronize with the rotation of the rotating gantry 12. The X-ray controller 21, based on this synchronization pulse, controls the radiation timing of the X-rays to synchronize with the rotation of the rotating gantry 12.

In addition, based on the control information and the synchronization pulse, the X-ray controller 21 specifies the radiation conditions of the X-rays, more specifically, the tube voltage, the tube current, the radiation period, and the radiation timing of the X-rays, and generates information indicating the radiation conditions. Subsequently, the photon energy distribution of the X-rays to be radiated is specified.

The X-ray controller 21 outputs, to the voltage control information generator 22, information for controlling the tube voltage among the information indicating the radiation conditions of the X-rays (for example, the change amount of the tube voltage along the time sequence, the change cycle, and the control timing). The operations thus far are the same as those in the first embodiment.

Subsequently, based on the information indicating the radiation conditions of the X-rays, the X-ray controller 21 generates dose setting signals for setting the dose of the X-rays to be radiated from the X-ray source 13. It should be noted that as this information indicating the dose of X-rays, for example, the desired dose of the X-rays may be set by an operator as the radiation conditions of the X-rays via the scan controller 100; alternatively, predetermined values may be set and stored as the radiation conditions of the X-rays. In addition, the dose setting signals are preferably signals that indicate the dose which is constant against the change in the tube voltage, although it may be signals indicating a range in which the dose is changed within an allowable range. The X-ray controller 21 outputs the generated dose setting signals to the grid control information operating unit 281.

The measuring unit 280 is provided in a position that does not block the X-rays radiated from the X-ray source 13 to the subject and at a dose in which the X-rays that have been radiated from the X-ray source 13 yet have not been transmitted through the subject can be measured. For example, in FIG. 1, the measuring unit 280 is provided in the vicinity of the X-ray source 13. It should be noted that the measuring unit 280 may be provided any location, as long as the measuring unit 280 can measure the dose of X-rays that have not been transmitted through the subject, for example, at one end of the X-ray detector 15.

The measuring unit 280 measures the dose of X-rays radiated from the X-ray source 13. The measuring unit 280 outputs the signals indicating the measured dose of X-rays to the grid control information operating unit 281.

The grid control information operating unit 281 receives, from the X-ray controller 21, the dose setting signals of the desired dose. In addition, the grid control information operating unit 281 receives, from the measuring unit 280, signals indicating the dose of the X-rays actually radiated and measured. The grid control information operating unit 281 compares these signals, and based on this comparison result, feedback controls the grid controller 25 in such a manner that the dose of the X-rays radiated from the X-ray source 13 to be the dose indicated by the dose setting signals.

Figure 5:
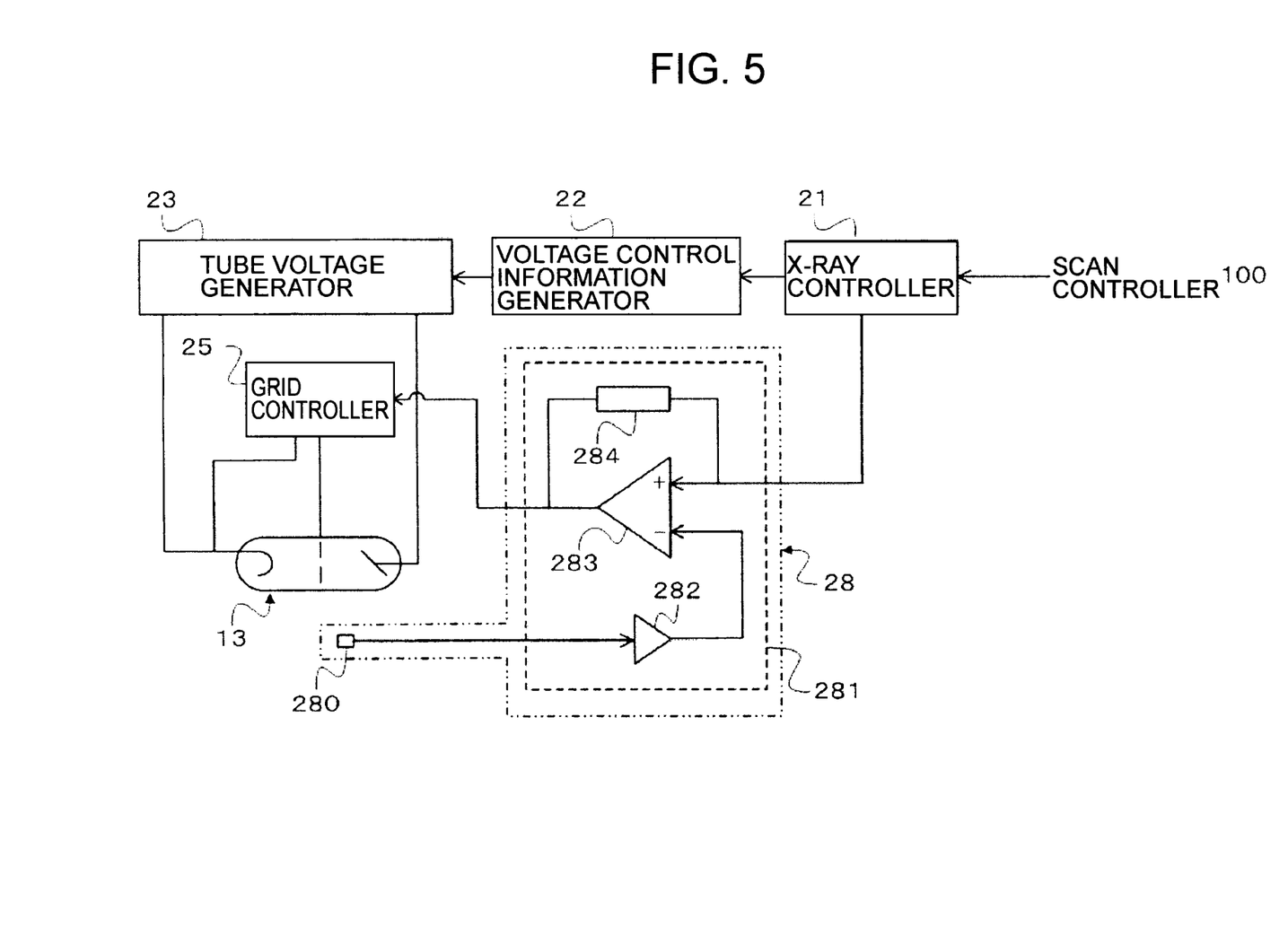
FIG. 5 is a diagram illustrating one example of the configuration of a grid control information operating unit according to the second embodiment.

Here, with reference to FIG. 5, the detailed configuration of the grid control information operating unit 281 will be described. FIG. 5 is a diagram illustrating one example of the detailed configuration of the grid control information operating unit 281. As illustrated in FIG. 5, the grid control information operating unit 281 includes an amplifier 282, an error amplifier 283, and a phase compensator 284.

The amplifier 282 receives, from the measuring unit 280, signals indicating the dose of the X-rays measured at the actual radiation, and amplifies the signals. The amplifier 282 then outputs the amplified signals to the error amplifier 283.

The error amplifier 283 receives the dose setting signals from the X-ray controller 21. In addition, the error amplifier 283 receives the signals indicating the measured dose of the X-rays amplified from the amplifier 282. The error amplifier 283 amplifies the comparison results of these signals, that is, the signal difference of the difference between these signals, outputs the amplified signal difference to the grid controller 25, and thereby, causes the grid controller 25 to feedback control the signal difference to be zero. In short, the grid controller 25 is allowed to feedback control so that the measured dose to be equal to the dose indicated by the dose setting signals. It should be noted that the phase compensator 284 stabilizes the feedback control system related to the dose including the error amplifier 283.

The grid controller 25 receives, from the grid control information operating unit 281 (namely, the error amplifier 283), the signal difference as the comparison result of the comparison between the dose setting signals and signals indicating the measured dose of the X-rays. The grid controller 25 controls the grid voltage based on the signal difference. Hereinafter, one example of the operation focusing on the control of the grid voltage relating to the feedback control will be described.

If the tube voltage is low, the dose of the X-rays radiated from the X-ray source 13 is small, resulting in the output of signals measured in the measuring unit 280 and amplified by the amplifier 282 also being small. In this case, the signal difference between signals output by the amplifier 282, which is the output of the error amplifier 283, and the dose setting signals increase in the positive direction. In other words, the voltage in the direction of increasing the tube current based on the characteristics of FIG. 2A is mapped on a grid. In this case, the error amplifier 283 causes the grid controller 25 to control the voltage of the grid so that the output difference between the dose setting signals and the signals output by the amplifier 282 become small. That is, based on the increase in signal difference from the error amplifier 283 in the positive direction, the grid controller 25, in FIG. 2A, increases the voltage of the grid to the cathode in the positive direction (in the 0 voltage direction in FIG. 2A), thereby increasing the tube current and the dose.

In addition, if the tube voltage is high, the dose of the X-rays radiated from the X-ray source 13 is large, resulting in the output of signals measured in the measuring unit 280 and amplified by the amplifier 282 also being large. In this case, the signal difference between the signals output by the amplifier 282, which is the output of the error amplifier 283, and the dose setting signals increases in the negative direction. In other words, the voltage in the direction of decreasing the tube current based on the characteristics of FIG. 2A is mapped on a grid. In this case as well, the error amplifier 283 causes the grid controller 25 to control the voltage of the grid so that the output difference between the dose setting signals and the signals output by the amplifier 282 becomes small. That is, based on an increase in the signal difference from the error amplifier 283 in the negative direction, the grid controller 25, in FIG. 2A, increases the voltage of the grid to the cathode in the negative direction (in the 0 voltage direction in FIG. 2A), thereby decreasing the tube current and the dose.

Consequently, the grid controller according to the second embodiment controls the grid in the same pattern as in Graph G13 having the grid control voltage waveform pattern in FIG. 2B, as in the first embodiment.

It should be noted that by combining the present embodiment and the first embodiment, two controls may be operated. That is, the grid voltage is controlled in the grid control voltage waveform pattern G13 (refer to FIG. 2B) on the one hand, as illustrated in the first embodiment; while, on the other hand, as illustrated in the second embodiment, the grid voltage is feedback controlled so that the detection result of the actual dose to be the desired dose. In this case, if control by the method of the first embodiment still fails to achieve the desired dose, the under- and over-dose will be offset and controlled by the method of the second embodiment. Hence, as mentioned above, single usage of the feedback control of the second embodiment covers all of Graph G13 in the grid control voltage waveform pattern; however, the use of the two controls allows the feedback control to only control the abovementioned under- and over-dose, resulting in a small dynamic range and a fast loop response speed of the feedback control system.

The above operations measure the dose of the X-rays radiated from the X-ray source 13 to control the tube current so as to maintain the dose within a predetermined range, thereby directly controlling the X-ray intensity. Consequently, even in the event that the tube voltage is changed along the time sequence, the dose is controlled to be within a predetermined range, thereby flattening the photon energy distribution of the braking X-rays. That is, as in the first embodiment, a photon energy distribution of a desired width can be achieved, the dose rate (X-ray intensity) can be maintained within a predetermined range, and unnecessary exposure upon an increase in the tube voltage can be prevented.

It should be noted that in the second embodiment, the dose is actually measured and controlled to be the desired value (or range); however, the tube current can also be actually measured and controlled.

The embodiments of the present invention were set forth; however, the embodiments described above were presented as examples and are not intended to limit the range of the invention. These new embodiments may be carried out in various other configurations, and various abbreviations, replacements, and changes may be made in a range not departing from the summary of the invention. These embodiments and deformations thereof are included in the range and summary of the invention and included in the invention described in the range of patent claims as well as the range of the equivalent thereof.

What is claimed is:

1. An X-ray CT apparatus, comprising:
    an X-ray tube configured to radiate X-rays onto a subject;
    a detector including multiple detection elements configured to detect photons forming the X-rays;
    a tube voltage generator configured to apply a tube voltage to the X-ray tube while changing the tube voltage of the X-ray tube in a predetermined voltage changing cycle;
    a tube current controller configured to decrease a tube current upon an increase in the tube voltage and increase the tube current upon a decrease in the tube voltage; and
    a data acquisition system configured to acquire a flattened photon energy distribution of the X-rays radiated from the X-ray tube by acquiring an integrated value of a photon energy distribution during a predetermined data acquisition cycle longer than the voltage changing cycle.

2. The X-ray CT apparatus according to claim 1, wherein the tube current controller includes a grid controller configured to control a grid voltage of the X-ray tube to decrease the tube current upon an increase in the tube voltage and control the grid voltage to increase the tube current upon a decrease in the tube voltage.

3. The X-ray CT apparatus according to claim 2, wherein the grid controller is configured to control the grid voltage based on control information previously generated corresponding to a change in the tube voltage in the cycle.

4. The X-ray CT apparatus according to claim 2, wherein the grid controller includes a measuring unit configured to measure a dose of the X-rays radiated from the X-ray tube, so that the grid voltage is controlled so as to have the dose of the X-rays in a predetermined range based on the measured dose.

5. An X-ray CT apparatus, comprising:
    an X-ray tube configured to radiate X-rays onto a subject;
    a detector including multiple detection elements configured to detect photons forming the X-rays;
    a tube voltage generator configured to apply a tube voltage to the X-ray tube while changing the tube voltage of the X-ray tube in a predetermined voltage changing cycle; and
    a data acquisition system configured to acquire a flattened photon energy distribution of the X-rays radiated from the X-ray tube by acquiring an integrated value of a photon energy distribution during a predetermined data acquisition cycle longer than the predetermined voltage changing cycle by gradually changing the tube voltage and controlling a high voltage time in the tube voltage and a low voltage time in the tube voltage.

* * * * *